United States Patent [19]

Frank et al.

[11] Patent Number: 4,755,604

[45] Date of Patent: Jul. 5, 1988

[54] PREPARATION OF 3-METHYLPIPERIDINE

[75] Inventors: Gerhard Frank, Hirschberg; Gerald Neubauer, Weinheim, both of Fed. Rep. of Germany

[73] Assignee: BASF Aktiengesellschaft, Fed. Rep. of Germany

[21] Appl. No.: 62,408

[22] Filed: Jun. 15, 1987

Related U.S. Application Data

[63] Continuation of Ser. No. 641,858, Aug. 17, 1984, abandoned.

[30] Foreign Application Priority Data

Aug. 17, 1983 [DE] Fed. Rep. of Germany ....... 3329692

[51] Int. Cl.$^4$ .................. C07D 211/12; C07D 211/02
[52] U.S. Cl. .................................... 546/184; 540/612; 548/579
[58] Field of Search ........................ 540/612; 546/184; 548/579

[56] References Cited

U.S. PATENT DOCUMENTS

| | | | |
|---|---|---|---|
| 2,200,282 | 5/1940 | Lazier | 546/184 X |
| 2,790,804 | 4/1957 | Silverstone | 546/184 |
| 3,082,067 | 3/1963 | Hund | 23/200 |

FOREIGN PATENT DOCUMENTS

| | | | |
|---|---|---|---|
| 1486890 | 9/1977 | United Kingdom | 564/511 |
| 1488335 | 10/1977 | United Kingdom | 546/184 |

*Primary Examiner*—Richard A. Schwartz
*Attorney, Agent, or Firm*—Keil & Weinkauf

[57] ABSTRACT

5-Membered, 6-membered or 7-membered cyclic imines are prepared by hydrogenating a $C_2$–$C_4$-alkanedinitrile in the liquid phase, at from 180° to 300° C. and under superatmospheric pressure, in the presence of a catalyst, by a process in which an iron catalyst obtained by reduction of an iron oxide with hydrogen at $\leq 500°$ C. is used.

6 Claims, No Drawings

PREPARATION OF 3-METHYLPIPERIDINE

This application is a continuation of application Ser. No. b 641,858, filed on Aug. 17, 1984, now abandoned.

German Published Application DAS No. 2,514,004 discloses that cyclic imines, such as 3-methylpiperidine, are obtained by hydrogenating 2-methylglutarodinitrile in the liquid phase in the presence of ammonia and of a nickle catalyst. However, the yield of 3-methylpiperidine in this process is unsatisfactory. Moreover, the conventional process gives substantial amounts of polyamines having a relatively high degree of condensation.

It is an object of the present invention to provide a process for the preparation of 5-membered, 6-membered or 7-membered cyclic imines which gives high yields and in which very small amounts of highly condensed polyamines are formed and the catalyst has a long life.

We have found that this object is achieved by a process for the preparation of 5-membered, 6-membered or 7-membered cyclic imines, which possess one imino group a 4 to 6 carbon atoms in the ring and in which one or more carbon atoms can carry alkyl of 1 to 4 carbon atoms as a substituent, by hydrogenation of a $C_2$–$C_4$-alkanedinitrile, in which one or more carbon atoms can have alkyl of 1 to 4 carbon atoms as a substituent, in the liquid phase, at from 180 to 300° C. and under superatmospheric pressure, in the presence of a catalyst, wherein an iron catalyst obtained by reduction of an iron oxide with hydrogen at $\leq 500°$ C. is used.

The novel process has the advantages that relatively high yields of cyclic imines are obtained, the presence of ammonia is not required, the amount of highly condensed polyamines obtained is reduced and the catalyst used has a long life. The novel process is noteworthy in that, at above 200° C., greater amounts of polyamines having a relatively high degree of condensation were expected to be formed.

The starting materials used are $C_2$–$C_4$-alkanedinitriles in which one or more carbon atoms can carry alkyl of 1 to 4 carbon atoms as a substituent. Preferred $C_2$–$C_4$-alkanedinitriles are those which carry methyl or ethyl as a substituent on a carbon atom. Examples of suitable starting materials are succinodinitrile, 2-ethylsuccinodinitrile, glutarodinitrile, 2-methylglutarodinitrile, adipodinitrile and trimethyladipodinitrile, 2-methylglutarodinitrile being particularly important.

Although the presence of ammonia is not required, liquid ammonia can be used concomitantly in the reaction, from 1 to 12 parts by volume of ammonia advantageously being employed per part by volume of dinitrile. The hydrogenation is carried out with hydrogen at elevated temperatures. The process is carried out at from 180 to 300° C., in particular from 200° to 260° C., advantageously under from 150 to 320 bar. The pressure and temperature conditions are of course chosen so that the hydrogenation takes place in the liquid phase. Furthermore, it has proven useful to recycle from 1 to 15, in particular from 6 to 10, parts by volume of crude hydrogenation mixture per part by volume of freshly introduced dinitrle. In addition to containing unconverted dinitrile, a hydrogenation mixture of this type contains, for example, the corresponding cyclic imine, alkanediamine and small amounts of products having a relatively high degree of condensation; a typical hydrogenation mixture contains, for examle, principally 3-methylpiperidine, together with a small amount of 2-methyl-1,5-diaminopentane, a small amount of methylglutarodinitrile, other unspecified amines, and ammonia from the cyclization reaction, and may contain liquid ammonia if this has been used.

The catalyst used, according to the invention, is an iron catalyst obtained by reduction of an iron oxide with hydrogen at $\leq 500°$ C. Suitable catalysts are described in, for example, German Laid-Open Application DOS No. 2,429,293.

Catalysts which have proven particularly useful are molded metallic iron catalysts obtained from anisometric iron oxide particles by reduction with hydrogen at $\leq 500°$ C., and containing a lubricant. Advantageously, the metallic iron particles exhibit a degree of reduction of $\geq 95\%$. The degree of reduction is the amount, in per cent, of available now present in metallic form. Preferably used starting materials are anisometric γ-iron oxides, in particular γ-iron(III) oxide and γ-iron(III) oxide hydroxide, the latter compound, which is known under the name lepidocrocite, being particularly preferably employed. It can be obtained by, for example, the process described in German Published Application DAS Nos. 1,061,760. The anisometric iron oxides have, for example, a mean particle length of from 0.1 to 2, preferably from 0.2 to 1.2, μm, a length:thickness ratio of from 5:1 to 40:1, and a BET specific surface area of from 25 to 28 $m^2/g$. The products obtained by heating the stated iron(III) oxides may also be used, the treatment advantageously being carried out at from 250 to 700° C.

The molded iron catalyst materials additionally contain lubricants, for example inorganic substances having a framework structure, eg. talc or, in particular, graphite. Advantageously, the molded catalysts contain lubricants in an amount of from 1 to 5% by weight, based on the total catalyst material comprising iron particles and lubricants. Graphite has proven a particularly useful lubricant. The molded iron catalyst material therefore essentially consists of metallic iron particles, a small amount of iron oxide, depending on the degree of reduction of the iron particles, and a lubricant. The said catalyst material, for example in the form of spheres, tablets or extrudates, advantageously has an indentation hardness of $\geq 300$ kp/$cm^2$.

The preferably used molded iron catalyst materials are advantageously prepared starting from, for example, a γ-iron(III) oxide, in particular γ-iron(III) oxide hydroxide (lepidocrocite). The products obtained by heating the stated iron(III) oxides may also be used, the heat treatment advantageously being carried out at from 250 to 700° C. Iron(III) oxide hydroxide is obtained, for example, from an aqueous solution of an iron salt, by precipitation with sodium hydroxide solution by a process as described in German Published Application DAS No. 1,061,760. Advantageously, the γ-iron oxide hydroxide particles are washed until the alkali content is less than 0.1% by weight, calculated as sodium oxide. The acicular iron(III) oxide particles are reduced by means of hydrogen, in a fluidized bed, in a rotary tubular oven or, preferably, in a stirred fixed bed, for example at from 260° to 500° C., in particular from 300° to 450° C., in the course of from 3 to 36 hours. Advantageously, a dry stream of hydrogen is employed, and a relatively high hydrogen flow rate is maintained. It has proven useful to use not less than a 60-fold excess of hydrogen. The reduction is advantageously carried out until the degree of reduction is $\geq 95\%$. Acicular metal particles essentially consisting of iron and obtained in this manner still substantially posses the shape of the starting materials and, in spite of the above transformation reaction, are homogeneous.

The metal particles thus obtained are then stabilized. In this procedure, the metal particles are enveloped in an oxide layer by controlled oxidation, in order to eliminate the pyrophoricity due to the large free surface area of the small particles. This is achieved by passing a gas containing molecular oxygen, for example an air/nitrogen mixture, over the metal powder, while strictly maintaining a temperature preferably not exceeding 100° C., in particular not exceeding 80° C. After the stabilization procedure, the degree of reduction should not be less than 80%, preferably not less than 90%. The stabilization procedure, the degree of reduction should not be less than 80%, preferably not less than 90%. The stabilized iron particles have a BET surface area of from 4 to 25, preferably from 8 to 12, $m^2/g$, lengths of from 0.05 to 2.0 $\mu m$, and pore volumes of less than 0.4 $cm^3/g$, the ratio of micropores to macropores being from 1:6 to 1:10, in favor of the macropores.

The iron particles stabilized in this manner are mixed with an inert lubricant, preferably graphite. Advantageously, from 2 to 5% by weight of lubricant is used. Processing of the mixture of stabilized iron particles and lubricant to give moldings, for example pressing of the said mixture to give tables, is advantageously carried out under nitrogen. The indentation hardness of the moldings should be $\geq 300$ kp/cm$^2$. The resulting moldings are activated by treatment with a relatively large, eg. a 60-fold, excess of hydrogen at $\leq 500°$ C., preferably from 300 to 460° C., under atmospheric or superatmospheric pressure, eg. from 100 to 150 bar. In this procedure, the degree of reduction achieved is advantageously $\geq 95\%$. The activation procedure increases the indentation hardness of the moldings from, for example, 300 to 600–800 kp/cm$^2$.

The hydrogenation of the dinitrile can be carried out by batchwise procedure, but it is advantageous to carry out the reaction continuously, for example by a trickle-bed procedure using a fixed-bed iron catalyst.

The cyclic imine produced is obtained in pure form by distilling the hydrogenation mixture, if necessary after evaporating the ammonia. 3-Methylpiperidine is used as a vulcanization accelerator and an additive to lubricants, and is also an intermediate for the prepartion of nicotinic acid, which is important as a feed additive.

The Examples which follow illustrate the process according to the invention

EXAMPLE 1

Preparation of the catalyst 600 kg of acicular lepidocrocite ($\gamma$-FeOOH), whose chlorine content and Na$_2$O content are each less than 0.1% by weight and which is prepared as described in German Published Application DAS No. 1,061,760 and has a specific surface area of 32 m$^2$/g, a mean needle length of 0.8 $\mu$m, a needle length:needle thickness ratio of 22:1, a bulk density of 0.37 g/cm$^3$ and a pH of 7.2, are reduced in a stirred fixed bed at 400° C. for 38 hours with 400 m$^3$ (S.T.P.) of hydrogen to give metallic iron (Fe $\geq 95\%$), a 64-fold stoichiometric excess of hydrogen being used. The pyrophoric acicular metal pigment is then enveloped in a stabilizing oxide layer by means of a nitrogen/air mixture at 60° C.; the degree of reduction should not fall below 90%. The yield is 400 kg. The iron particles have a BET specific surface area of 7.2 m$^2$/g, and an electron micrograph shows that they possess an anisotropic geometrical form (acicular or rod-shaped). To prepare moldings having a diameter of 5 mm and a height of 4 mm, the stabilized pulverulent metal pigment is mixed with 2% by weight of graphite, and the mixture is tableted under nitrogen. The indentation hardness of the tablets should not be less than 300 kp/cm$^2$.

Hydrogenation of 2-methylglutarodinitrile 3 liters of a molded iron catalyst obtained as described above are placed in a tube reactor having a length of 2 m and an internal diameter of 45 mm. The catalysts is activated by treatment with hydrogen for 24 hours at 360° C. Using a trickle-bed procedure, 0.8 liter/hour of 2-methylglutarodinitrile, 0.8 liter/hour of liquid ammonia and 4.6 liters/hour of crude hydrogenation mixture, as well as hydrogen, are then fed in. The hydrogenation is carried out under 260 bar and at 230° C. After the ammonia has been evaporated, gas chromatographic analysis shows that the crude hydrogenation product contains 93% by weight of methylpiperidine. By means of distillation, and determination of the residue, a content of 0.6% by weight of oligome of 2-methylpentamethylenediamine is established.

EXAMPLE 2

The tube reactor and catalyst described in Example 1 are used. At a reactor temperature of 230° C., 0.8 liter/hour of 2-methylglutarodinitrile and 6.4 liters/hour of the crude hydrogenation mixture obtained are fed into the stated reactor.

Analysis of the crude hydrogenation mixture by gas chromatography gives the following result:

0.4% by weight of methylpentylamine,
98.7% by weight of 3-methylpiperidine,
0.8% by weight of 2-methylpentamethylenediamine and
0.03% by weight of 2-methylglutarodinitrile.

Distillation gives 0.2% of relatively high boiling compounds which cannot be determined by gas chromatography; the selectivity with respect to 3-methylpiperidine is therefore 98.5%.

EXAMPLE 3

1.2 liters/hour of a mixture consisting of 90% by weight of 2-methylglutarodinitrile and 10% by weight of ethylsuccinodinitrile are fed into the reactor described in Example 1, and over the catalyst described in that Example. A hydrogenation temperature of 240° C. and a hydrogen pressure of 260 bar are maintained, and 7.8 liters hour of the crude hydrogenation mixture are recycled to the reactor.

Analysis of the crude hydrogenation mixture by gas chromatography gives the follwing result:

3% by weight of monoamines,
89% by weight of 3-methylpiperidine,
5% by weight of 2-ethylpyrrolidine,
0.3% by weight of diamines and
0.02% by weight of unconverted dinitirels.

Distillation gives 0.6% of relatively high boiling compounds (or residues) which cannot be determined by gas chromatography; the selectivity is therefore 98.2% with respect to 3-methylpiperidine and 69.7% with respect to 2-ethylpyrrolidine, corresponding to a total selectivity of 95.3%.

EXAMPLE 4

0.8 liter/hour of ethylsuccinodinitrile is fed into the reactor described in Example 1, and over the catalyst described in that Example. A hydrogenation temperature of 190° C. and a hydrogen pressure of 260 bar are maintained, and 7.8 liters/hour of the hydrogenation mixture obtained under these conditions are recycled to the reactor.

Analysis by gas chromatography gives the following result:

96.5% by weight of 2-ethylpyrrolidine,
2.3% by weight of 2-ethyltetramethylenediamine,
0.01% by weight of 2-ethylsuccinonitrile and
1.2% by weight of monoamines and relatively high boiling compounds.

EXAMPLE 5

0.4 liter/hour of adipodinitrile, 1.2 liter/hour of ammonia and 2.4 liters/hour of hydrogenation mixture are fed, at 270° C. and under an $H_2$ pressure of 260 bar, into the reactor described in Example 1, and over the catalyst described in that Example. Azacycloheptane is obtained in a yield of 70% together with 3% of bishexamethylenetriamine, 7% of hexylamine and 15% of hexamethylenediamine.

We claim:

1. A process for the preparation of 3-methylpiperidine which comprises: hydrogenating 2-methylglutarodinitrile in the liquid phase at from 180° to 300° C. and under a pressure of 150 to 320 bar in the presence of a molded metallic iron catalyst which is obtained from anisometric iron oxide particles by reduction with hydrogen at 500° C., such molded iron catalyst having a content of 1 to 5% by weight of graphite and an indentation hardness of $\geq 300$ kp/cm$^2$, and concomitant use of from 1 to 15 parts by volume of crude hydrogenation mixture per part by volume of 2-methylglutarodnitrile, such crude hydrogenation mixture containing principally 3-methylpiperidine together with small amounts of 2-methyl-1,5-diaminopentane, 2-methylglutarodinitrile, ammonia and unspecified amines.

2. The process of claim 1, wherein the metallic iron particles exhibit a degree of reduction of $\geq 95\%$.

3. The process of claim 1, wherein the molded metallic iron catalyst has an indentation hardness of from 600 to 800 kp/cm$^2$.

4. The process of claim 1, wherein anisometric $\gamma$-iron(III)-oxidenhydroxide is used as starting material for the catalyst.

5. The process of claim 1, wherein a temperature of 200° to 260° C. is maintained.

6. The process of claim 1, wherein from 6 to 10 parts by volume of crude hydrogenation mixture are concomitantly used per part by volume of 2-methylglutarodinitrile.

* * * * *